(12) United States Patent
Binder

(10) Patent No.: US 10,201,497 B2
(45) Date of Patent: *Feb. 12, 2019

(54) TREATMENT OF MIGRAINE HEADACHES WITH PRESYNAPTIC NEUROTOXIN

(71) Applicant: Miotox, LLC, Beverly Hills, CA (US)

(72) Inventor: William J. Binder, Beverly Hills, CA (US)

(73) Assignee: Miotox, LLC, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/582,407

(22) Filed: Apr. 28, 2017

(65) Prior Publication Data

US 2017/0232080 A1 Aug. 17, 2017

Related U.S. Application Data

(63) Continuation of application No. 14/410,010, filed as application No. PCT/US2013/000131 on May 10, 2013, now abandoned, which is a continuation of application No. 13/478,640, filed on May 23, 2012, now Pat. No. 8,722,060, and a continuation of application No. 13/478,602, filed on May 23, 2012, now Pat. No. 8,617,569, and a continuation of application No. 13/478,922, filed on May 23, 2012, now abandoned, and a continuation of application No. 13/478,828, filed on May 23, 2012, now Pat. No. 8,420,106, and a continuation of application No. 13/478,876, filed on May 23, 2012, now Pat. No. 8,491,917.

(60) Provisional application No. 61/609,817, filed on Mar. 12, 2012.

(51) Int. Cl.
*A61K 9/00* (2006.01)
*A61K 38/16* (2006.01)
*A61K 38/48* (2006.01)

(52) U.S. Cl.
CPC .......... *A61K 9/0085* (2013.01); *A61K 9/0019* (2013.01); *A61K 38/164* (2013.01); *A61K 38/48* (2013.01); *A61K 38/4893* (2013.01); *C12Y 304/24069* (2013.01)

(58) Field of Classification Search
CPC .... A61K 9/0085; A61K 38/48; A61K 38/164; A61K 9/0019; A61K 38/4893; C12Y 304/24069
See application file for complete search history.

(56) References Cited

U.S. PATENT DOCUMENTS

| | | | |
|---|---|---|---|
| 5,714,468 A | 2/1998 | Binder | |
| 5,721,215 A | 2/1998 | Aoki et al. | |
| 6,265,379 B1 | 7/2001 | Donovan | |
| 6,358,926 B2 | 3/2002 | Donovan | |
| 6,458,365 B1 | 10/2002 | Aoki et al. | |
| 6,806,251 B2 | 10/2004 | Lamb | |
| 7,270,287 B2 | 9/2007 | First | |
| 7,491,403 B2 | 2/2009 | Borodic | |
| 7,655,244 B2 | 2/2010 | Blumenfeld | |
| 7,704,511 B2 | 4/2010 | Turkel et al. | |
| 7,981,433 B2 | 7/2011 | Blumenfeld | |
| 8,420,106 B1 | 4/2013 | Binder | |
| 8,491,917 B1 | 7/2013 | Bender | |
| 8,617,569 B2 | 12/2013 | Binder | |
| 8,722,060 B2 | 5/2014 | Binder | |
| 8,883,143 B2 | 11/2014 | Binder | |
| 2001/0025024 A1 | 9/2001 | Donovan | |
| 2004/0204471 A1 | 10/2004 | Seibert | |
| 2004/0247606 A1 | 12/2004 | Borodic et al. | |
| 2005/0106183 A1 | 5/2005 | Lamb | |
| 2005/0147625 A1 | 7/2005 | First | |
| 2006/0276510 A1 | 12/2006 | Abu-Shakra et al. | |
| 2008/0003242 A1 | 1/2008 | First | |
| 2008/0069841 A1 | 3/2008 | Panjwani | |
| 2008/0279895 A1 | 11/2008 | Blumenfeld | |
| 2009/0263426 A1 | 10/2009 | Turkel et al. | |
| 2010/0189655 A1 | 7/2010 | Turkel et al. | |
| 2010/0227822 A1 | 9/2010 | Blumenfeld | |
| 2011/0200639 A1 | 8/2011 | Blumenfeld | |

FOREIGN PATENT DOCUMENTS

| | | |
|---|---|---|
| CA | 2596366 A1 | 8/2006 |
| JP | 2007509953 A | 4/2007 |
| JP | 2008528685 A | 7/2008 |
| WO | 2004084839 A2 | 10/2004 |
| WO | 2005084705 A1 | 9/2005 |
| WO | 2006083455 A1 | 8/2006 |

(Continued)

OTHER PUBLICATIONS

Weiss et al. Post-Traumatic Migraine: Chronic Migraine Precipitated by Minor Head or Neck Trauma. Headache. Jul. 1991;31(7):451-6 Abstract only p. 1 (Year: 1991).*
Allergan Inc., BOTOX Product Information, pp. 1-2 (2016).
Anonymous, PTSD—Does anyone else deal with chronic daily headache from PTSD, how do you treat them?, www.drugs.com/answers/post-traumatic-stress-disorder-does-snyone-else-408139. pp. 1-5 (2011).
Blumenfeld, et al., Procedures for Administering Botulinum Toxin Type A for Migraine and Tension-type Headache, Headache 43: 884-891 (2003).
EPO, Search Report, EP13760304.9, dated Mar. 4, 2015.

(Continued)

*Primary Examiner* — Taeyoon Kim
(74) *Attorney, Agent, or Firm* — UltimatEdge IP Law Group, P.C.; Dean G. Stathakis

(57) ABSTRACT

The present invention provides a method for treating a patient for migraine headache, including symptoms associated with migraine head ache, such as migraine associated vertigo, which comprises administering to the patient a therapeutically effective amount of an invertebrate presynaptic neurotoxin, e.g. Botulinum toxin in a pharmaceutically safe form.

22 Claims, 2 Drawing Sheets

(56) References Cited

FOREIGN PATENT DOCUMENTS

WO    2010135538 A1    11/2010

OTHER PUBLICATIONS

PCT Form ISA 237, Written Opinion, PCT/US2013/000131, dated Aug. 6, 2013.
PCT Form IB 373 International Preliminary Report on Patentability, PCT/US2013/000131, dated Sep. 16, 2014.
Albanese, "Terminology for Preparations of Botulinum Neurotoxins", JAMA, Jan. 5, 2011, vol. 305, No. 1, p. 89-90.
Bach-Rojecky, et al., "Central Origin of the Antinociceptive Action of Botulinum Toxin Type A", Pharmacology, Biochemistry and Behavior 94 (2009) 234-238, Elsevier, Inc.
Bahl, "Local Anesthesia in Dentistry", Anesth Prog 51:138-142 (2004), American Dental Society of Anesthesiology.
Binder, et al., Facial Plastic Surgery Clinics of North America 11, 465-475 (2003).
Binder, et al., Otolaryngology-Head and Neck Surgery vol. 123, No. 6, 669-676 (2000).
Blumenfeld, et al., "Method of Injection of Onabotulinumtoxin for Chronic Migraine: A Safe, Well-Tolerated, and Effective Treatment Paradigm Based on the PREEMPT Clinical Program", Headache, 2010 American Headache Society, ISSN 0017-8748; doi: 10.111/j.1526-4610.2010.01766.x, Wiley Periodicals, Inc.
Blumenfeld, et al_, "Procedures for Administering Botulinum Toxin Type A for Migraine and Tension-type Headache," Headache, Aug. 17, 2003, vol. 43, p. 884-891.
Day, "Sphenopalatine Ganglion Analgesia", Current review of Pain 1999, 3:342-347 (Abstract Only).

European Search Report, Application No. EP13760304.9, dated Mar. 4, 2015.
Gerwin, "Treatment of Chronic Migraine Headache with OnabotulinumtoxinA", Current Pain and Headache Reports, Current Science Inc., New York, vol. 15, No. 5, May 6, 2011 p. 336-338.
Goadsby, "Sphenopalatine (pterygopalatine) ganglion stimulation and cluster headache: New hope for ye who enter here", Cephalagia, 2013, p. 1-3.
International Search Report, PCT/US2013/000131, dated Aug. 6, 2013.
Malamed, et al., "Intraoral Maxillary Nerve Block: An Anatomical and Clinical Study", Anesthesia Progress, Mar./Apr. 1983, pp. 44-48.
Niamtu, "Local Anesthetic Blocks of the Head and Neck for Cosmetic Facial Surgery, III: Techniques for the Maxillary Nerve, Cosmetic Dermatology", vol. 17, No. 10, Oct. 2004, p. 645-647.
Robertson, et al., "Critical analysis of the use of onabotulinumtoxinA (botulinum toxin type A) in migraine", Neuropsychiatric Disease and Treatment, Dove Medical Press (NZ) Ltd. vol. 8, Jan. 1, 2012 p. 35-48.
Shone, et al., "Peptide substrate specificity and properties of the zinc-endopeptidase of botulinum type B neurotoxin", Eur. J. Biochem. 225, 263-270 (1994).
BOTOX Information (2016), p. 1-2.
Channell et al, "Manangement of Chronic Post traumatic Headache: A Multidisciplinary Approach," JAOA, Bol. 109, No. 9, Sep. 2009, pp. 509-513.
PTSD—"Does anyone else deal with chronic daily headache from PTSD, how do you treat them?" PTSD webpage from Drugs.com, (2011). Downloaded from www.drugs.com/answers/post-traumatic-stress-disorder-does-snyone-else-408139, p. 1-5.

* cited by examiner

TREATMENT OF MIGRAINE HEADACHES WITH PRESYNAPTIC NEUROTOXIN

This application is a continuation that claims priority and the filing date pursuant to 35 U.S.C. 120 to U.S. patent application Ser. No. 14/410,010, filed Dec. 19, 2014, a U.S. Non-Provisional Patent Application filed pursuant to 35 U.S.C. § 371 from International Patent Application PCT/US2013/000131, filed May 10, 2013, which claims priority to U.S. Non-Provisional patent application Ser. No. 13/478,640, filed May 23, 2012, now U.S. Pat. No. 8,722,060; U.S. Non-Provisional patent application Ser. No. 13/478,602, filed May 23, 2012, now U.S. Pat. No. 8,617,569; U.S. Non-Provisional patent application Ser. No. 13/478,922, filed May 23, 2012, now abandoned; U.S. Non-Provisional patent application Ser. No. 13/478,828, filed May 23, 2012, now U.S. Pat. No. 8,420,106; U.S. Non-Provisional patent application Ser. No. 13/478,876, filed May 23, 2012, now U.S. Pat. No. 8,491,917; and U.S. Provisional Patent Application 61/609,817, filed Mar. 12, 2012.

BACKGROUND OF THE INVENTION

1. Field of the Invention

The present invention provides a method for treating migraine headaches and conditions associated therewith.

2. Background of the Art

Botulinum toxins have been used to treat migraine headache. This is well established in the art. By way of example only, see U.S. Pat. Nos. 5,714,468; 5,721,215; 6,458,365; 7,655,244; 7,704,511 and 7,981,433. All of these references are to be incorporated herewith in their entirety. These patents include: Binder; Botulinum toxin injections to the head for migraine, Blumenfeld; Botulinum toxin injections to the sphenopalatine ganglion, nasal approach and vascular approach, suture line technique (these are not foramina or exit points); Aoki; Tension type headache treatment with Botulinum toxin, and Turkel; 31 sites as for the FDA approved protocol for chronic migraine.

Onabotulinumtoxin A has been FDA approved for chronic migraine, and the dose used is 155 to 195 units, with a dilution of 2 cc per 100 units of onabotulinumtoxin A. Doses ranging from 25 units to 260 units have been used to treat various headache disorders. These have involved intramuscular injections in fixed sites and follow the pain sites.

Botulinum toxin side effects are usually due to local diffusion to surrounding muscles producing unwanted weakness.

SUMMARY OF THE INVENTION

The present invention provides a method for treating migraine headaches and conditions associated therewith, e.g. migraine associated vertigo (MAV). In particular, the present invention comprises a method for treating a patient for migraine headache which comprises administering to the patient a therapeutically effective amount of an invertebrate presynaptic neurotoxin in a pharmaceutically safe form. (It is noted that, as used herein, "invertebrate presynaptic neurotoxin" refers to both invertebrate toxins and biologically active peptide fragments of proteinaceous invertebrate toxins.)

In a first aspect of the invention, there is provided a method for selection and treatment of externally caused migraine headache, said method comprising:

identifying a patient group having migraine headache;
of the identified patient group, determining a specific patient with a post traumatic migraine headache; and
administering to the selected patient a therapeutically effective amount of an invertebrate presynaptic neurotoxin in a pharmaceutically safe form to the selected patient's head.

In a second aspect of the invention, there is provided a method for treating a human patient with migraine headache, said method comprising:

administering to the patient a therapeutically effective amount of an invertebrate presynaptic neurotoxin in a pharmaceutically safe form;
the administration being on the trigeminal cervical system, for enabling transport of the neurotoxin from distal to central sites, said administration comprising extramuscular injection of the neurotoxin over the aponeurotic fascia of the scalp for enabling the neurotoxin to diffuse into distal sensory nerves, in order to enable concentration over the occipital-parietal-frontal head region.

In a third aspect of the invention, there is provided a method for treating a human patient with migraine headache, said method comprising:

administering to the patient a therapeutically effective amount of an invertebrate presynaptic neurotoxin in a pharmaceutically safe form;
the administration comprising intra-oral extramuscular injection of the neurotoxin in a foramina of the sphenopalatine ganglion for enabling diffusion of the neurotoxin to the ganglion; and
the administration being on the trigeminal cervical system, enabling axonal transport of the neurotoxin from distal to central sites.

In a fourth aspect of the invention, there is provided a method for treating a human patient with migraine headache, said method comprising:

administering to the patient a therapeutically effective amount of an invertebrate presynaptic neurotoxin in a pharmaceutically safe form; and
the administration comprising extramuscular injection of the neurotoxin to emerging nerve points in the face and neck including foraminal sites for enabling the neurotoxin access to concentrated nerve bundles at exit points of the foramina.

Finally, in a fifth aspect of the invention, there is provided a method for reducing the symptoms of migraine associated vertigo, or vertiginous migraine, comprising administering to a human having said vertigo a therapeutically effective amount of a presynaptic neurotoxin in a pharmaceutically safe form.

In each aspect of the invention described above, the method of the invention is preferably directed to the treatment of chronic migraine headache.

The following limitations are preferred in the method of the present invention:

The method of the present invention wherein the presynaptic neurotoxin is a Botulinum toxin. More particularly, in the method of the present invention, the Botulinum toxin may be Botulinum Toxin A, B, C, D, E, F, or G.

The method of the invention wherein the Botulinum toxin is Botulinum toxin A.

The method of the invention wherein the neurotoxin comprises an Endotoxin.

The method of the invention wherein the Endotoxin is an endopeptidase derived from Botulinum toxin.

Preferably, the Botulinum toxin is diluted with saline, e.g. normal saline. More preferably, Botulinum toxin is diluted to at least about 1 cc saline per 100 units of Botulinum toxin, e.g. from about 1 cc to 10 cc saline per 100 units of Botulinum toxin.

In general, the present invention aims to minimize the Botulinum toxin side effects present with prior injection techniques and uses a novel injection approach to achieve this goal. In addition, this invention aims to increase the efficacy across multiple headache types including chronic and episodic migraine, post-traumatic headache, post-craniotomy headache, tension type headache and medication overuse headache. This invention focuses the medication on the sites of maximal benefit; i.e., the trigemino-cervical nerves.

Thus, the present invention is preferably directed to treating migraine headaches with Botulinum toxin (and/or endopeptidase) by adjusting the toxin concentration and volume to establish optimum diffusion of toxin in non-muscle related areas of the head and neck, or exit points of nerves therein. This method avoids side effects such as muscle paralysis and reduces doses overall by use of high concentration/low volume injections at nerve exit points which also results in reduction of injection pain due to less rapid tissue expansion upon injection.

BRIEF DESCRIPTION OF THE DRAWING FIGURES

The advantages and features of the present invention will be better understood by the following description when considered in conjunction with the accompanying drawings, in which.

DETAILED DESCRIPTION OF THE INVENTION

Figure 1:
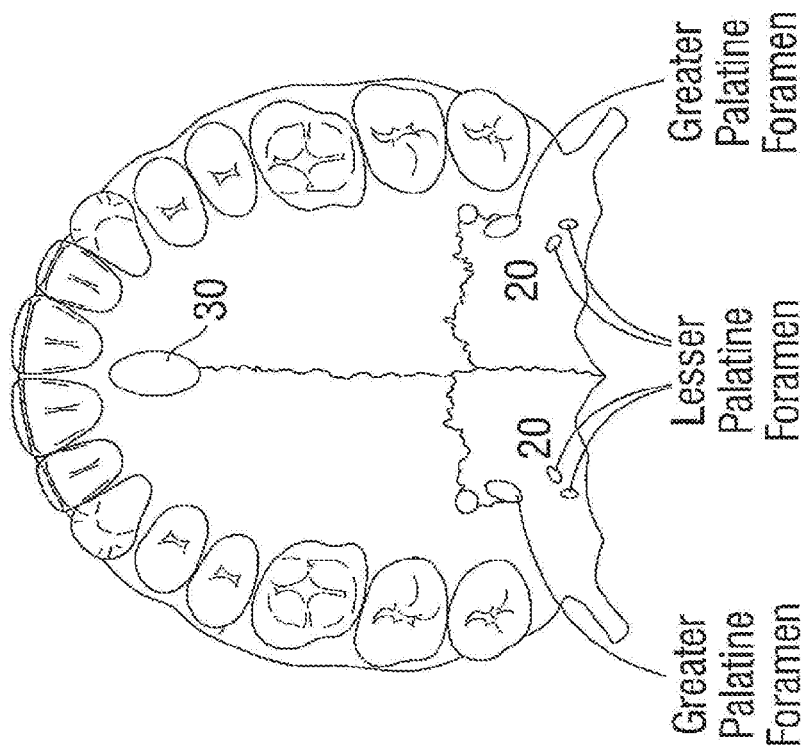
FIG. 1 is a diagram of injection sites in accordance with the present invention showing the frontal (10), parietal (20), and occipital (30) aponeurotic fascia in head 14.

Regarding the first aspect of the invention noted above, trauma has been documented to increase frequency of migraine headache and is a risk factor for conversion from episodic to chronic migraine.

Anxiety and depression are more often associated with chronic migraine than episodic migraine, while trauma may be implicated in initiating or worsening migraine. There are a number of different trauma modalities that can be involved in this process such as:

1. Closed head injury, this includes blast injuries
2. Open head injury, with intra-parenchymal lesions such as hematomas and contusions
3. Post craniotomy with trauma secondary to surgical effects as well as the underlying condition
4. Psychological trauma, such as depression, anxiety, post traumatic syndrome and post-traumatic stress disorder (PTSD)
5. Whiplash injury as well as other soft tissue injuries around the head and neck area The International Headache Society classifies post-traumatic headache and migraine separately. The post-traumatic headache requires that the headache start within one week of the trauma. If the headache persists for less than 3 months after this it is referred to as an Acute Post-Traumatic headache. If the headache persists for longer than 3 months it is referred to as a Chronic Post-Traumatic headache. These headaches are further sub-divided into mild, moderate or severe depending on the extent of the injury that caused the headache. In addition there is a category for headaches attributed to whiplash injury. The actual features of the post-traumatic headache are not described in the classification but these can resemble migraine features. Furthermore episodic migraine can transform to chronic migraine as a result of head trauma. In these cases there is a prior history of migraine, which increases in frequency after the trauma.

It has been reported that nearly forty-percent (40%) of soldiers had migraines or probable migraines during their tours of duty, but few had a history of migraines before their deployments. In accordance with the present invention, a patient group can be identified by survey. For example, nineteen percent (19%) of the 2,687 soldiers surveyed upon return from duty met the criteria for definite migraines, eighteen percent (18%) had probable migraines, and eleven percent (11%) non-migraine-type headaches. Those with definite migraines had an average of 3.5 migraine days/month.

Just five percent (5%) of the soldiers had a history of migraine headaches prior to their deployments to Iraq.

As an example, after returning home from Iraq, soldiers are sent through a medical processing site. Members of one brigade completed a validated 17-question survey about headaches. Based on their survey responses, soldiers were divided into three groups: definite migraines, probable migraines, or non-migraine headaches, a system of classification similar to that used in the American Migraine Study.

The mean age of respondents was 27. The group was ninety-five percent (95%) male and five-percent (5%) female.

Soldiers rated their migraine headaches as a mean 6.5 on a 10-point severity scale, lasting an average of 5.2 hours. Yet only 2% received triptans, the standard of care for the treatment of acute migraines.

Findings from a 3-month follow-up survey indicate that many soldiers continue to have elevated rates of migraines after their return stateside.

The method in accordance with the present invention for selection and treatment of externally caused migraine headache generally includes identifying a patient group having migraine headache, and of the identified patient group, determining a specific patient with a post-traumatic migraine headache. Thereafter, the selected patient is administered with a therapeutically effective amount of an invertebrate presynaptic neurotoxin in a pharmaceutically safe form to the selected patient's head.

The present invention is also directed to treating post-traumatic migraine headaches with Botulinum toxin (and/or endopeptidase) by adjusting the toxin concentration and volume to establish optimum diffusion of toxin in non-muscle related areas of the head and neck, such as fascia injections to the scalp or exit points of nerves in the mouth and neck. This improvement, e.g., use of high concentration/low volume injections at nerve exit points and low concentration/high volume injections in fascia on the scalp, avoids side effects such as muscle paralysis and reduces doses overall.

Thus, in the first aspect of the invention, as described above, the present invention includes but is not limited to closed head injury, including blast injuries; open head injury, with intra-parenchymal lesions such as hematomas and contusions, post craniotomy with trauma secondary to surgical effects; psychological trauma, such as depression, anxiety and post-traumatic stress disorder; and whiplash injury as well as other soft tissue injuries around the head and neck area.

The administration advantageously includes, but is not limited to. extramuscular injection of the neurotoxin of suitable dilution (a) over the aponeurotic fascia to enable the neurotoxin to diffuse into distal sensory nerves, in order to concentrate the neurotoxin over the occipital-parietal-frontal head region, or (b) intra-orally, in a foramina of the sphenopalatine ganglion for enabling diffusion of the neurotoxin to the ganglion, or (c) to emerging exit points of nerves including foraminal sites for enabling more concentrated dilution of the neurotoxin access to concentrated nerve bundles at exit points of the foramina.

Regarding the second aspect of the invention noted above, the present invention is directed to treatment of migraine headaches, which may or may not have resulted from post traumatic stress, with Botulinum toxin (and/or endopeptidase) by adjusting the toxin concentration and volume to establish optimum diffusion of toxin in non-muscle related areas of the head, such as fascia injections to the scalp. This method of treatment avoids side effects such as muscle paralysis and reduces doses overall, through the use of low concentration/high volume injections in fascia on the scalp.

In general, dilute Botulinum toxin: about 4 to 10 cc saline per 100 units of Botulinum toxin is injected over the aponeurotic fascia, not into muscle, allowing the toxin to diffuse into distal sensory nerve endings that are concentrated over the occipital parietal-frontal head regions. (There is no muscle in this location) No muscle weakness results as all the injections are in non-muscular regions. The toxin diffuses in a broad area due to the dilution; allowing for a decrease in the number of injection sites. Botulinium toxin is delivered to the distal sensory nerve endings 10 in the scalp 14. See FIG. 1. These include unmyelinated C fibers.

Importantly, the present invention utilizes the proximal axonal transport of Botulinum toxins from distal to central sites.

Regarding the third aspect of the invention, noted above, dilute Botulinum toxin: about 1 cc saline per 100 of Botulinum toxin units, is injected in the sphenopalatine ganglion, allowing the toxin to diffuse into distal sensory nerve endings. This method of treatment may, also, be used to treat migraine headaches that result from post-traumatic stress or otherwise. (There is no muscle in this location). Alternatively, the toxin is injected in a foramina of the sphenopalatine ganglion. No muscle weakness results as all the injections are in non-muscular regions.

Figure 2:
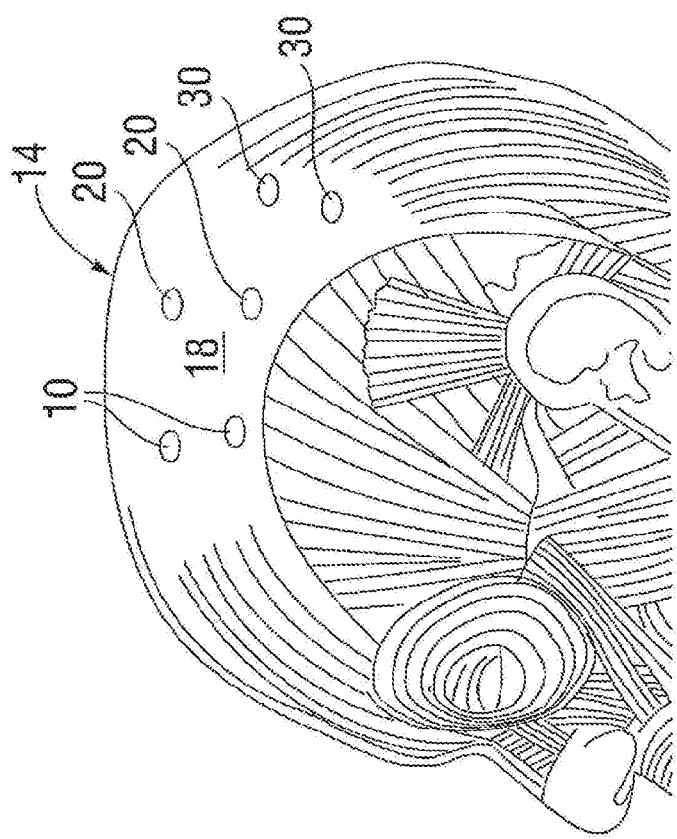
FIG. 2 is a diagram of injection sites in accordance with the present invention; and refers specifically to the greater and lesser palatine foramen (20) which are nerve exit points for the palatine nerve and the incisive foramen (30) a nerve exit point for the nasopalatine nerve.

Intra-oral injections are done in the region of the foramina of the sphenopalatine ganglion. This allows diffusion of toxin to the ganglion without a deep injection through muscle. Thus, lower doses can be used. There is no risk of muscle trauma including intra-muscular hemorrhage related to needles tracking through muscle to reach the sphenopalatine ganglion. The dilution for these injections is preferably about 1 cc saline per 100 units of Botulinum toxin, to prevent diffusion to other intra-oral structures. See FIG. 2.

There are two possible intra-oral approaches to the sphenopalatine ganglion. Again, see FIG. 2. The first intraoral method involves needle insertion in the region of the mucobuccal fold (not shown) at the maxillary second molar and advancing the needle in a posterior, superior, and medial direction, into the region of the pterygopalatine fossa. The second intra-oral approach to the sphenopalatine ganglion 20 is through the greater palatine canal. The opening of this is located between the middle of the second molar and the middle of the third molar. This site will be approximately 7 mm from the end of the hard palate.

In regards to the fourth aspect of the invention, noted above, this invention uses the same methods of administration described in the procedures, above, to deliver endotoxins to the same sites to treat migraine headaches resulting from post traumatic stress or otherwise. Endotoxins do not cause muscle weakness as they are targeted to sensory nerves, however the current technique of intra-muscular injections can still cause side effects related to needle trauma of muscle and the need to do multiple injections.

In general, a method for treating a patient with migraine headache in accordance with the fourth aspect of the present invention includes administering to the patient a therapeutically effective amount of an invertebrate presynaptic neurotoxin in a pharmaceutically safe form. The administration includes extramuscular injection of the neurotoxin to emerging nerve points in the head and neck for enabling the neurotoxin access to concentrated nerve bundles at exit points of the foramina.

Finally, regarding the fifth aspect of the invention relates to the treatment of migraine associated vertigo. Migraine-associated vertigo (MAV) or vertiginous migraine is a recognized disease condition consisting of dizziness and/or vertigo. Other terms used to describe this condition include vestibular migraine, migrainous vertigo, or migraine-related vestibulopathy. While thought to be related to migraine headache, patients diagnosed with MAV and the like do not have classic migraine headaches, or have chronic non-specific headaches that do not fit into the migraine classification developed by the International Headache Society.

Persons with MAV often describe chronic dizziness and disequilibrium in the form of a "rocking" sensation. Sometimes the vertiginous effects are described as episodes of rotational vertigo, changes in vision, visual "snow", nausea and severe motion intolerance. Neurological examinations (including neuroimaging) are often completely normal. Patients with chronic dizziness often do not experience acute rotational vertigo or even the pain of a migraine headache.

Commonly prescribed medications for vertigo include meclizine hydrochloride (Antivert), diphenhydramine (Benadryl), scopolamine transdermal patch (Transderm-Scop) and promethazine hydrochloride (Phenergan).

Thus, there is provided a method for reducing the symptoms of migraine associated vertigo, or vertiginous migraine, comprising administering to a human having said vertigo a therapeutically effective amount of a presynaptic neurotoxin in a pharmaceutically safe form, wherein the method comprises using any of the injection techniques of aspects 2 through 4 to administer a presynaptic invertebrate neurotoxin, e.g. Botulinum toxin, to reduce the symptoms of migraine associated vertigo, or vertiginous migraine.

The invention further includes the following methods of treatment of migraine headache:

The method of the present invention, wherein the neurotoxin is delivered to the face, cranium, and neck.

The method of the present invention wherein the externally caused migraine headache is post-traumatic stress disorder (PTSD).

The method of the present invention wherein the externally caused migraine headache is traumatic brain injury (TBI).

Current injection techniques known in the art today use a system of flooding the potential structures involved with migraine pathogenesis with the medication, but this may lead to unwanted side effects. This invention avoids this by targeting the sites of most benefit, i.e., see FIGS. 1-3, with the most efficiency. The technique also utilizes adjustments in concentrations to establish diffusion of medication in non-muscle related areas.

Importantly, the present invention utilizes the proximal axonal transport of Botulinum toxins from distal to central sites.

The technique, in accordance with the present invention, involves 3 different modalities of administration to allow for maximizing the dose and thus the effect on the trigeminal cervical system and sphenopalatine ganglion system; while minimizing the side effects.

Injection Modalities

1. Dilute Botulinum toxin: about 4 to 10 cc per 100 units is injected over the aponeurotic fascia, not into muscle, allowing the toxin to diffuse into distal sensory nerve endings that are concentrated over the occipital-parietal-frontal head regions. (There is no muscle in this location). No muscle weakness results as all the injections are in non-muscular regions. The toxin diffuses in a broad area due to the dilution; allowing for a decrease in the number of injection sites. Botulinum toxin is delivered to the distal sensory nerve ending in the scalp. See FIG. 1.

2. Intra-oral injections are done in the region of the foramina of the sphenopalatine ganglion, this allows diffusion of toxin to the ganglion without a deep injection through muscle. Thus, lower doses can be used. There is no risk of muscle trauma including intra-muscular hemorrhage related to needles tracking through muscle to reach the sphenopalatine ganglion. The dilution for these injections is about 1 cc per 100 units of Botulinum toxin, to prevent diffusion to other intraoral structures. See FIG. 2.

3. Emerging nerve points which include foraminal injection sites and foraminal injection sites deep to the muscle layer allows Botulinum toxin access to the concentrated nerve bundles at the exit points and thus lower doses with improved efficacy and less side effects and adverse events can be achieved. The cervical plexus emerges from the posterior portion of the sternomastoid muscle and injections at this site can encompass the entire distribution of the cervical plexus. The dilution for these injections is about 1 cc per 100 units of Botulinum toxin. The concentrated solution prevents diffusion to local muscle and the accurate needle placement allows the medication to be delivered to the site where it will most effective. See FIG. 3.

Figure 3:
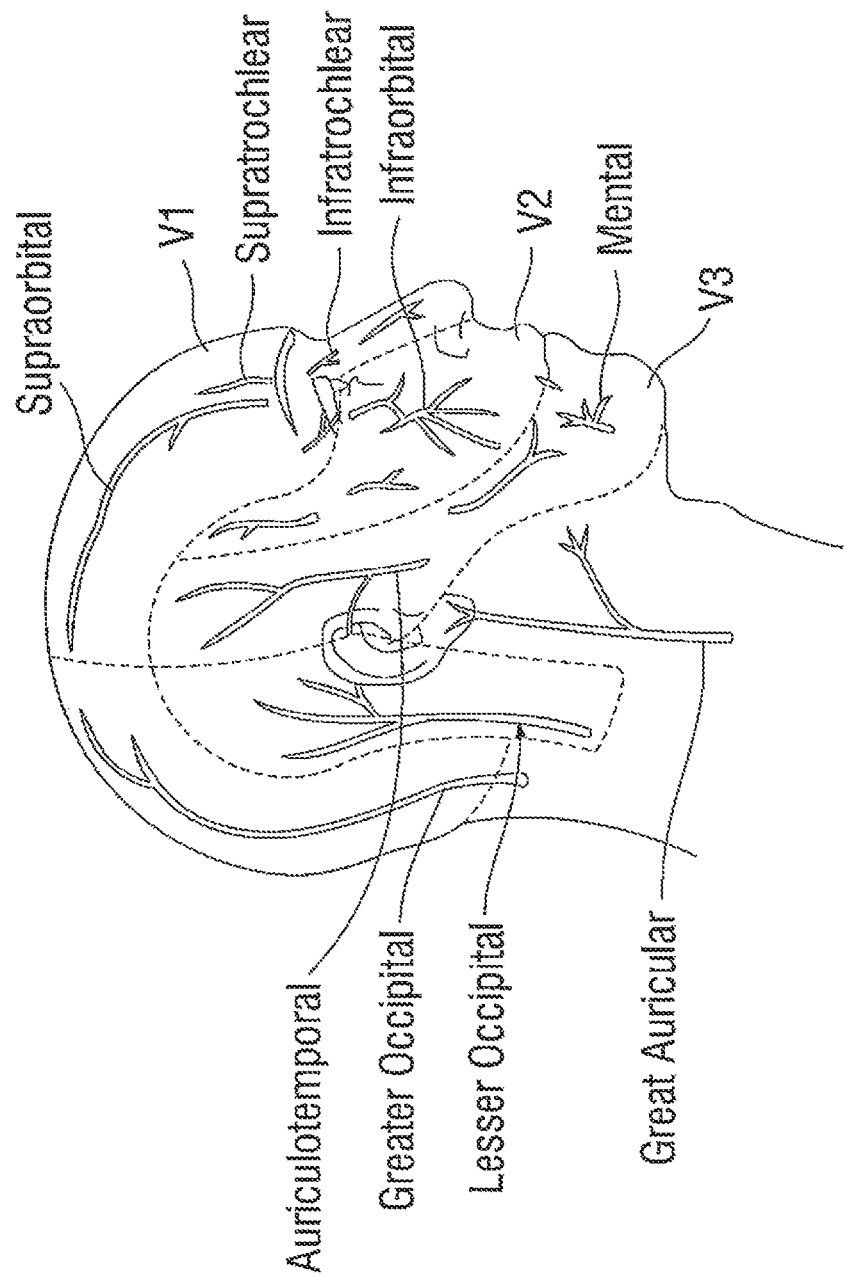
FIG. 3 illustrates suitable nerve exit points in the head and neck.

With reference to FIG. 3, sensory branches of the trigeminal nerves (ophthalmic V1, maxillary V2 and mandibular V3) leave the skull through three separate foramina; in the following order: the superior orbital fissure, the foramen rotundum, and the foramen ovale.

V1 carries information from the scalp (forehead to vertex) upper eyelid and eye, nose and nasal mucosa, meninges and frontal sinuses.

V2 carries information from lower eyelid, cheek, upper lip, dentition, mouth meninges and sinuses (ethmoid and sphenoid).

V3 carries information from lower lip, dentition, jaw, external ear, meninges.

Note all 3 divisions supply the meninges.

By way of illustration, injections are made at sites 10 on a scalp 14 on each side of the aponeurotic fascia 18 with a 4-10 cc dilution allowing for a broad diffusion of the Botulinum toxin, see FIG. 1. However, for the forminal and emerging nerve bundle injections a 1 cc dilution is used to prevent diffusion to surrounding muscles, see FIGS. 2 and 3.

The foraminal anatomy is as follows:
Frontal region-supraorbital foramen-supra-orbital nerve
  Supratrochlear foramen-supratrochlear nerve
Maxilla-incisive foramen-nasopalatine nerve (Septum)
Palatine-greater and lesser palatine foramen-greater and lesser palatine nerves
Maxilla-Inferior orbital fissure/foramen-zygomatic and infra-orbital nerves and orbital branch of the pterygo-palatine ganglion (SPG).

There are two possible intra-oral approaches to the Sphenopalatine ganglion. See FIG. 2. The first intra-oral method involves needle insertion in the region of the mucobuccal fold (not shown) at the maxillary second molar and advancing the needle in a posterior, superior, and medical direction, into the region of the pterygopalatine fossa. The second intra-oral approach to the Sphenopalatine ganglion 20 is through the greater palatine canal. The opening of this is located between the middle of the second molar and the middle of the third molar. This site will be approximately 7 mm from the end of the hard palate.

The following examples are intended to illustrate but not limit the present invention.

Clinical Examples

First Aspect

Case 1

18-year old male returns from Iraq where he sustains a blast closed head injury and since that time has daily headaches that have features suggestive of migraine headache. He fails to respond to tricyclic antidepressants and biofeedback courses. Onabotulinum toxin is injected using the FDA approved protocol for onabotuliumtoxinA. He tolerates the procedure well. He has no side effects. After 10 weeks he reports no further headaches.

Case 2

22-year old male returns from Iraq where he sustains a blast closed head injury and since that time has daily headaches that have features suggestive of migraine headache. He fails to respond to tricyclic antidepressants and biofeedback courses. He meets criteria for chronic migraine complicated by medication overuse headache. He also fails to respond to numerous preventive medications such as Topiramate and Propranolol. He is treated with onabotulinumtoxinA using the PREEMPT injection protocol with fixed sites and follow-the-pain injections. Total dose given 195 units. He develops neck pain, brow ptosis and shows no improvement in headache frequency after three (3) treatment cycles.

He is then treated with the variable concentration focused injection protocol as outlined in this invention.

OnabotulinumtoxinA is diluted as follows: 100 units in 8 cc of normal saline (0.1 ml contains 1.25 units) and 100 units in 1 cc of normal saline (0.1 ml contains 10 units).

Injection Sites and Dosing as Follows 8 cc dilution
Frontal aponeurotic fascia 5 units each side
Parietal aponeuotic fascia 5 units each side
Occipital aponeurotic 5 units each side
Sub-total 30 units 1 cc Dilution
Orbital ridge supro-medial angle over supra-trochlear and supra-orbital nerves 5 units each side
Infraorbital foramen 5 units each side
Mental foramen 5 units each side
Posterior aspect, mid-section of sternocleidomastoid muscle 5 units each side
Occipital foramen 5 units each side Auriculotemporal nerve just anterior and inferior to the tragus 5 units each side Intra-oral muscosal injection superior to second molar intra-oral 5 units each side Sub-total 60 units Total dose given 100 units.

Lower dosing of onabotulinumtoxinA is used as the medication is delivered in a focus where it will have the most benefit; i.e.: no unnecessary flooding of medication to unwanted sites. 20 injections are done instead of the more conventional 39. None of these sites match the approved PREEMPT injection protocol for migraine. He tolerates the procedure well. He has no side effects. The patient does not develop neck weakness or pain as the neck musculature is not injected. The patient does not develop brow ptosis as the frontalis muscle is not injected. After 10 weeks he reports no further headaches.

Case 3

19-year old male, returns from Iraq with a history of migraine headaches present on 4 days out of each week. He was in Iraq for over a year, but during this time he did not sustain any injuries in particular no head injury. Prior to deployment he did not suffer with headaches. His current headaches are generalized, throbbing in nature, associated with nausea and photo-phobia. They interfere with his ability to work. He is assessed as having chronic migraine triggered by stress relating to his deployment. He is successfully treated with onabotulinumtoxinA in accordance with the injection methodology set forth in Case 1.

Case 4

28-year old woman is involved in a motor vehicle accident with blunt head trauma that results in an acute left epidural hematoma. She undergoes urgent craniotomy. The hematoma is evacuated via a left prieto-temporal craniotomy. She gradually recovers but her course is complicated by ongoing headaches overt the left hemicranium. These are throbbing in nature, interfere with her activities, and associated with nausea and vomiting. These headaches are present on a near daily basis. She is successfully treated with onabotulinumtoxinA in accordance with the injection methodology as outlined in case 1 above.

Aspect 2

Case 1

43-year old woman, with a long standing history of migraine, suffers with headache on twenty (20) days out of each month and requires triptan medication on twelve (12) days out of each month to try and control her more disabling headaches. She meets criteria for chronic migraine complicated by medication overuse headache. She fails to respond to numerous preventive medications such as Topiramate and Propranolol. She is treated with onabotulinumtoxinA using the PREEMPT injection protocol with fixed sites and follow-the-pain injections. Total dose given 195 units. She has developed neck pain, brow ptosis and no improvement in her headache frequency after three (3) treatment cycles.

She is then treated with the focused injection protocol as outlined in this invention.

OnabotulinumtoxinA is diluted as follows: 100 units in 8 cc of normal saline (0.1 ml contains 1.25 units).

Injection Sites and Dosing as Follows 8 cc dilution

Frontal aponeurotic fascia 5 units each side (0.4 cc per side)

Parietal aponeurotic fascia 5 units each side (0.4 cc per side)

Occipital aponeurotic 5 units each side (0.4 cc per side)

Total dose: 30 units

The patient reports fewer migraine headaches of lesser duration and intensity. The patient does not develop neck weakness or pain as the neck musculature is not injected. The patient does not develop brow ptosis as the frontalis muscle is not injected.

Lower dosing of onabotulinumtoxinA is used as the medication is delivered in a focus where it will have the most benefit; i.e.: no unnecessary flooding or extravasation of medication to unwanted sites.

Case 2

38 year old man with a history of chronic migraine headaches is successfully treated with onabotulinumtoxinA using the PREEMPT injection sites. Unfortunately, he develops temporalis wasting which gives him an hour-glass appearance due to the toxin adversely affecting the temporalis muscle region. He is seen for consultation to review other treatment options. Because onabotulinumtoxinA treatments have been successful he wishes to continue with these but wants to avoid the side effects he experienced. He is successfully treated using the method of onabotulinumtoxinA outlined in the above invention.

100 units of onabotulinumtoxinA is diluted in 4 cc of normal saline. The more concentrated solution is chosen in this case to limit any possible diffusion to the temporalis muscle region. Each 0.1 ml contains 2.5 units of onabotulinumtoxin A.

Frontal aponeurotic fascia 5 units (2.5 units in 2 locations about 1 inch apart) on each side (0.2 cc).

Parietal aponeurotic fascia 5 units (2.5 units in 2 locations about 1 inch apart) on each side (0.2 cc).

Occipital aponeurotic fascia 5 units (2.5 units in 2 locations about 1 inch apart) on each side (0.2 cc).

Total of 30 units.

The treatment is well tolerated and the patient does not develop any temporalis wasting.

Case 3

64-year old bald man has a long history of migraines dating back to his teens. He now presents with headaches mainly involving the vertex of the head. These occur about 8 days a month. They are disabling, worsened by head movement and associated with sensitivity to light and noise. These are diagnosed as episodic migraine. His neurological examination and brain imaging studies are normal for age. The only exception is that he has senile ptosis.

Treatment options are reviewed with the patient. He wants to try a preventive approach to avoid getting these disabling headaches. He wants to try onabotulinumtoxinA. However, injections of the frontalis are contra-indicated as these will worsen the senile brow ptosis and in addition the headaches are only located over the vertex of the head.

OnabotulinumtoxinA is successfully used to treat his headaches using the method described in this invention.

100 units of onabotulinumtoxinA is diluted in 10 cc of normal saline. The toxin is dawn up into 1 cc syringes with a 30 gauge half inch needle used for administration to the vertex area of the head. The vertex is divided into a grid-like area with injections placed in the center of each square.

Each injection is 0.2 cc which contains 2 units of onabotulinumtoxinA: 10 cc dilution per 100 units (0.1 unit per 1 cc). The width of the square is one inch as this encompasses the diffusion area of this dilute toxin. The grid consists of 9 squares similar to a tic tac toe diagram with each square measuring one inch so that the total treated area is 3 inches by 3 inches. The injections are done in the center of each square and at the 4 outside corners for a total of 13 sites. The needle is inserted deep into the aponeurotic fascia. Total dose administered 26 units. The patient's headache frequency and intensity improve and there is no worsening of his senile brow ptosis.

Aspect 3

Case 1

43-year old woman, with a long standing history of migraine, suffers with headache on twenty (20) days out of each month and requires triptan medication on twelve (12) days out of each month to control her more disabling headaches. She meets criteria for chronic migraine complicated by medication overuse headache. She fails to respond to numerous preventive medications such as Topiramate and Propranolol. She is treated with onabotulinumtoxinA using the PREEMPT injection protocol with fixed sites and follow-the-pain injections. Total dose given 195 units. She develops neck pain, brow ptosis and no improvement in her headache frequency after three (3) treatment cycles.

She is then successfully treated with the injection protocol as outlined in this invention using OnabotulinumtoxinA diluted as follows: 100 units in 1 cc of normal saline. The injections are done with a 1 inch 30 gauge needle attached to a 1 cc syringe. The needle is inserted at 45 degrees angling the needle posteriorly, medially and superiorly with the entry point at the mucobuccal fold adjacent to the left maxillary second molar. 45 units are injected in the region of the left sphenopalatine ganglion and 45 units in a similar fashion in the region of the right sphenopalatine ganglion; for a total dose of 90 units. The patient does not develop neck weakness or pain as the neck musculature is not injected and the patient does not develop brow ptosis as the frontalis muscle is not injected.

Case 2

38-year old man presents with a long history of frequent episodic migraines. He averages 10-14 headache days per month. His headaches are side locked and only involve the right pen-orbital region. He works as a magician. He does not wish to use any medications that might interfere with his concentration, dexterity or facial expressions. As a result he is a poor candidate for oral preventive medications such as topiramate which can cause cognitive slowing, amitriptyline which can cause drowsiness, and Botox using the PREEMPT protocol as this could result in some loss of facial expression due to injections of the frontalis, corrugators and procerus muscles. He is successfully treated using the method of administration of onabotulinumtoxinA outlined in this invention, as follows:

100 units of OnabotulinumtoxinA is diluted with 1 cc of normal saline. The patient is lying with the head tilted far backwards and the mouth wide open so that the palate of the mouth is fully visible. A 27 gauge needle, 1.5 inches long is inserted 7 mm posterior to the edge of the hard palate in between the second and third molars angling upwards. 25 units is delivered in the region of the sphenopalatine ganglion bilaterally for a total of 50 units. The needle is inserted deep to the hard palate limiting any palatal weakness. The patient has no loss of facial expression from the delivery of onabotulinumtoxinA in this method.

Lower dosing of onabotulinumtoxinA is used as the medication is delivered in a focus where it will have the most benefit; i.e.: no unnecessary flooding of medication to unwanted sites.

Aspect 4

Case 1

43 year old woman, with a long standing history of migraine, suffers with headache on twenty (20) days out of each month and requires triptan medication on twelve (12) days out of each month to try and control her more disabling headaches. She meets criteria for chronic migraine complicated by medication overuse headache. She fails to respond to numerous preventive medications such as Topiramate and Propranolol. She is treated with onabotulinumtoxinA using the PREEMPT injection protocol with fixed sites and follow-the-pain injections. Total dose given is 195 units. She develops neck pain, brow ptosis and little improvement in her headache frequency after three (3) treatment cycles.

She is then treated with the injection protocol as outlined in this invention.

1 cc dilution: 100 units of Botulinum Toxin A in 1 cc saline

Orbital ridge supra-medial angle over supra-trochlear and supra-orbital nerves 5 units each side Infraorbital foramen 5 units each side Mental foramen 5 units each side Posterior aspect, mid-section of sternocleidomastoid muscle 5 units each side Occipital foramen 5 units each side Auriculotemporal nerve just anterior and inferior to the tragus 5 units each side Intra-oral muscosal injection superior to second molar intra-oral 5 units each side Total dose given 60 units.

The patient does not develop neck weakness or pain as the neck musculature is not injected. The patient does not develop brow ptosis as the frontalis muscle is not injected. The patient experiences less pain from the injections than from conventional treatment. The patient's migraine headache symptoms improve with less frequency and less intensity.

Lower dosing of onabotulinumtoxinA is used as the medication is delivered in a focus where it will have the most benefit; i.e.: no unnecessary flooding of medication and volume of diluents to unwanted sites.

Case 2

60 year old woman with frequent episodic migraine and severe needle phobia has been treated with onabotulinumtoxinA using the PREEMPT protocol in the past. Due to her needle phobia her method of treatment is changed with a focused delivered method of onabotulinumtoxinA at emerging nerve points. This method is chosen to limit side effects from intra-muscular injections and to achieve a high level of efficacy with the fewest possible needle insertions. The patient is treated lying down. Onabotulinumtoxin A is diluted with 1 cc of normal saline per 100 units; i.e.: 0.1 cc contains 10 units. At each injection site only 0.05 cc is delivered. The lower volume of onabotulinumtoxinA injection produces less discomfort due to less rapid expansion of tissue. A 31-gauge half-inch needle is used for administration. However a 30 gauge or 32 gauge needle can also be used. The following sites are injected:

The orbital bony ridge is palpated. Midway along the ridge the supra-orbital notch is palpable. This is a tender point and correlates with the emerging supra-orbital nerve. After injecting at this site the ridge is palpated over the supero-medial aspect, just adjacent to the nose, a tender point is located which correlates to the supra-trochlear nerve. This site is injected. The dosing at these two sites is: Orbital ridge supra-medial angle over supra-trochlear and supra-orbital nerves 5 units (0.05 cc) each site and this is repeated on the opposite side. Total dose given at these locations is 20 units.

Infra-orbital ridge is palpated. In line with the mid-pupillary point vertical line is followed inferiorly to a tender region located just below the orbital margin. This correlates with the emerging infra-orbital nerve. The dose injected at this site is 5 units (0.05 cc) and this is repeated on the opposite side. Total dose given at these sites is 10 units.

The patient is asked to rotate her head towards her shoulder and tilt the head downwards towards the chest. This activates the sternomastoid muscle. The muscle is palpated between the examiner's thumb and index fingers.

The examiner grips this muscle as the patient rotates the head back to the mid-line position. The posterior border of the muscle is palpated, and in the mid-section of the sternomastoid muscle a tender point is localized. This correlates with the emerging cervical rami, 10 units (0.1) is injected at this site and repeated on the opposite side. The total dose given at these sites is 20 units.

The Occipital foramen is palpated mid-way along the nuchal ridge between the occipital protuberance and the mastoid process. This is also a tender point and correlates to the emergence of the greater occipital nerve, 5 units of onabotulinumtoxinA, 0.05 cc are injected on each side in the same fashion. The total dose given at these sites is 10 units.

The emerging Auriculo-temporal nerve is injected just (a finger tip) anterior and inferior to the tragus and 5 units (0.05 cc) of onabotulinumtoxinA are given on each side. The total dose given to these sites is 10 units.

The total dose given to the patient for this treatment is 70 units.

The smaller needle size, the more concentrated onabotulinumtoxinA solution and the focused injection sites limit the pain associated with administration. The procedure is well tolerated and migraine headache symptoms are successfully treated.

Aspect 5
Case 1: Migraine Associated Vertigo

A 54 year old man presented with a long history of vertigo. The onset of vertigo began with minor episodes while the patient was in college. It then presented acutely with an incapacitating episode. The following year, the vertigo then recurred periodically. The patient then had an episode that lasted for 1 month with both symptoms of spinning and imbalance. The patient was worked up diagnostically by ear specialists, otologists, neurologists. Allergy testing was negative. Numerous CT and MRI scans and inner ear testing all proved to be normal with no evidence of tumors or vascular lesions. The diagnosis was confirmed by numerous specialists to be migraine associated vertigo or that of possible vascular origin. Treatment included various antihistamines such as diphenhydramine, meclizine hydrochloride, and scopolamine which did not control the symptoms of vertigo.

During the past 12 months, prior to initial consultation, the vertigo at times became incapacitating whereby the patient became confined to bed for periods of 24-48 hours. Over the last most 6 months, the patient experienced a frequency of two episodes of vertigo per month, each lasting 2-3 days, and then leaving the patient with prolonged periods of residual imbalance. The patient was recently treated with a trial of high dose Prednisone without success.

The initial treatment consisted of using OnabotulinumtoxinA with a dilution of 4 cc per 100 units. Each injection comprised between 0.1 cc (2.5 units) and 0.2 cc (5 units) which was applied to multiple sites over the glabella, forehead, temporal, occipital and suboccipital areas of the head and neck. In addition, the injections were applied to areas of the neck including the trapezius muscle. The number of units used in the initial treatment totaled approximately 150 units of OnabotulinumtoxinA. The patient was seen 3 months later and reported that the symptoms of vertigo were completely eliminated. The patient was then treated at consecutive periods of 3 month intervals with varying does between 150-175 units of OnabotulinumtoxinA. The vertigo was consistently eliminated with each treatment. The patient reported only one episode when the treatment period was extended beyond 4 months. The patient has continued OnabotulinumtoxinA injections as a preventive therapy for the vertigo.

Case 2

A 58 year old woman with chronic disabling vertigo presents for assessment and treatment. She has been diagnosed with otoliths in her semi-circular canals and any change in head position triggers vertigo. If she rolls over in bed, she awakens with severe vertigo. She has tried oral medications such as meclizine without benefit. She was treated with centrifugal force from an Otolaryngologist without change. Her brain MRI scans have all been normal.

She is treated with OnabotulinumtoxinA: 2 cc dilution per 100 units. Injections given as follows: 0.1 cc (5 units) injections in 5 sites in each temporalis muscle and area and 0.1 cc (5 units) in 5 sites in each occipitalis muscle and area. The procedure is well tolerated without side effects. Six weeks later she notes a progressive improvement in her vertigo. Initially greater stimuli are required to bring on the symptoms. At 12 weeks, she has her second OnabotulinumtoxinA treatment with the same sites and dosing. After this, she develops progressively more vertigo free days. As a result, she is able to return to work as a cashier.

The present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

The invention claimed is:

1. A method of treating a patient with a migraine headache caused by a traumatic brain injury comprising extramuscularly administering a therapeutically effective amount of a suitably diluted Botulinum toxin in a pharmaceutically safe form to the patient in need thereof to reduce the migraine headache caused by the traumatic brain injury.

2. The method of claim 1, wherein the Botulinum toxin is a Botulinum toxin A and/or a Botulinum toxin B.

3. The method of claim 2, wherein the Botulinum toxin A is onabotulinumtoxin A.

4. The method of claim 1, wherein the Botulinum toxin comprises an Endotoxin.

5. The method of claim 4, wherein the Endotoxin is an endopeptidase.

6. A method of treating a patient with a migraine headache caused by a traumatic brain injury comprising extramuscularly administering a therapeutically effective amount of a suitably diluted Botulinum toxin in a pharmaceutically safe form to the head of a patient in need thereof to reduce the migraine headache caused by a traumatic brain injury.

7. The method according to claim 6, wherein the Botulinum toxin is a Botulinum toxin A and/or a Botulinum Toxin B.

8. The method according to claim 7, wherein the Botulinum toxin A is onabotulinumtoxin A.

9. The method according to claim 6, wherein the Botulinum toxin is an Endotoxin.

10. The method of claim 9, wherein the Endotoxin is an endopeptidase.

11. A method of treating a patient with a migraine headache caused by a traumatic brain injury comprising extramuscularly administering to a patient in need thereof a therapeutically effective amount of a Botulinum toxin in a pharmaceutically safe form to the head and/or upper neck of the patient in need thereof to reduce the migraine headache caused by the traumatic brain injury;
- administration being on the sites of the trigeminal cervical system, enabling axonal transport of the Botulinum toxin from distal to central sites; and
- the administration comprising extramuscular injection of the Botulinum toxin of suitable dilution (a) over the aponeurotic fascia to enable the Botulinum toxin to diffuse into distal sensory nerves, in order to concentrate the Botulinum toxin over the occipital-parietal-frontal head region and/or (b) to emerging exit points of nerves including foraminal sites for enabling the Botulinum toxin access to concentrated nerve bundles at exit points of the foramina.

12. The method according to claim 11, wherein the administration to the aponeurotic fascia includes dilution of about 4-10 cc of normal saline per 100 units of Botulinum toxin.

13. The method according to claim 11, wherein the administrations according to (b) and (c) are at a dilution of about 1 cc normal saline per 100 units of Botulinum toxin.

14. The method according to claim 11, wherein the Botulinum toxin is Botulinum toxin A and/or a Botulinum toxin B.

15. The method according to claim 14, wherein the Botulinum toxin A is onabotulinumtoxin A.

16. The method according to claim 11, wherein the Botulinum toxin is an Endotoxin.

17. The method according to claim 16, wherein the Endotoxin is an endopeptidase.

18. The method according to claim 11, wherein the emerging nerve exit points are one or more of the Great auricular, Auriculotemporal, Supraorbital, Supratrochlear, Infratrochlear, Infraorbital or Mental nerve exit points.

19. The method according to claim 1, wherein the Botulinum toxin is extramuscularly administered into aponeurotic fascia and/or to emerging nerve exit points in the face and/or neck.

20. The method according to claim 19, wherein the emerging nerve exit points are one or more of the Great auricular, Auriculotemporal, Supraorbital, Supratrochlear, Infratrochlear, Infraorbital or Mental nerve exit points.

21. The method according to claim 6, wherein the Botulinum toxin is extramuscularly administered into aponeurotic fascia and/or to emerging nerve exit points in the face and/or neck.

22. The method according to claim 21, wherein the emerging nerve exit points are one or more of the Great auricular, Auriculotemporal, Supraorbital, Supratrochlear, Infratrochlear, Infraorbital or Mental nerve exit points.

* * * * *